United States Patent [19]

Brooker et al.

[11] 4,022,577

[45] May 10, 1977

[54] AUTOMATED RADIOIMMUNOASSAY

[75] Inventors: Gary Brooker; Wesley L. Terasaki; Michael G. Price, all of Charlottesville, Va.

[73] Assignee: The University of Virginia, Charlottesville, Va.

[22] Filed: Mar. 12, 1976

[21] Appl. No.: 666,302

[52] U.S. Cl. ............................. 23/230 B; 23/253 R
[51] Int. Cl.² .................. G01N 33/16; G01N 23/12
[58] Field of Search ............ 23/230 B, 253 R, 259; 424/1, 1.5; 195/127

[56] References Cited

UNITED STATES PATENTS

| 3,524,366 | 8/1970 | Hrdina ............................. 23/253 R |
| 3,679,312 | 7/1972 | Mansberg ........................ 23/253 R |
| 3,841,834 | 10/1974 | Gandhi et al. .................... 23/253 R |
| 3,876,374 | 4/1975 | Burns ................................ 23/253 R |

*Primary Examiner*—R.E. Serwin
*Attorney, Agent, or Firm*—Oblon, Fisher, Spivak, McClelland & Maier

[57] ABSTRACT

An automated radioimmunoassay apparatus which comprises:
  means for time controlled incubation of a multiplicity of sample solutions, each of which comprise a mixture of (a) a sample, possibly containing an antigen, intended to be assayed, (b) a solution of a known concentration of an antigen tagged with a radioactive isotope and (c) a solution of a known titer of an antibody reactable with said antigen;
  radioactivity detector means for providing a kinetic measurement of radioactivity as a solution is continuously passed therethrough, and for providing a static measurement of radioactivity as a solution is maintained statically within said detector;
  means for introducing said incubated sample into said radioactivity detector means;
  timing means, which is activatable by said radioactivity detector means when said detector means detects a predetermined threshold of radioactivity, for measuring time sequences and for generating control signals at predetermined time sequences;
  recording means coupled to said detector means for recording the amounts of radioactivity detected in said detector means;
  means for separating said kinetically measured solution into a first portion containing antigen which is unreacted with said antibody, and a second portion containing antigen reacted with said antibody;
  means for introducing one of said portions from said separating means into said radioactivity measuring means, for static detection;
  means for isolating said incubated sample from additional sample solutions introduced into said apparatus for assay, wherein said isolating means is activatable by a control signal emitted from said timing means, whereby said isolating means isolates the system at a first predetermined signal from said timing means, and whereby said isolating means reconnects the system to said incubation means at a second predetermined signal from said timing means, wherein the second predetermined time period is set so as to enable sufficient time to complete said static measurement before the next incubated sample arrives in the said detector means for the next sequential kinetic measurement; and
  means for flushing said sample from said system after static measurement thereof so as to prepare said detector for the next sequential sample for static measurement.

33 Claims, 12 Drawing Figures

AUTOMATED RADIOIMMUNOASSAY

The invention described herein was made in the course of or under a grant from the Department of Health, Education and Welfare.

BACKGROUND OF THE INVENTION

1. Field of the Invention

The present invention relates to a method for assaying the concentration of antigen in a sample by a radioimmunoassay technique. More particularly, the present invention relates to an automated radioimmunoassay technique for measuring antigen concentration via a selective antibody-antigen reaction, under conditions which permit extremely rapid analysis.

2. Description of the Prior Art

Isotope displacement using specific antibodies to measure minute quantities of insulin was first reported by Yalow et al (*Nature* 184, 1648) which has led to the widespread practice of this technique for the analysis of a wide variety of biologically important substances. Radioimmunoassay has become a primary technique for the routine analysis of literally hundreds of biochemical and clinically important substances. Radioimmunoassay is now the method of choice for the analysis of many substances, because antibodies with very high selectivity and affinity can be produced which permit measurement of any desired compound in rather impure samples. The amount of impurity can, in many cases, be $10^9$ times that of the substance of interest and not interfere with the measurement. This extraordinary selectivity and ability to detect femtomole ($10^{-15}$ mole) quantities of substances has pushed the radioimmunoassay to the forefront of modern analytical chemistry.

If the radioimmunoassay has any limitations at all, it is the amount of manual labor and time required to obtain results. A typical assay first involves the combination of the unknown sample or standard, specific isotope tracer and antibody. This solution is then incubated in the cold or at room temperature for at least 20-30 minutes to as long as several days to obtain equilibrium between the antigen (ligand molecule being measured) and the antibody. The antibody bound ligand isotope is then separated from the solution. This is generally accomplished by addition of dextran coated charcoal to absorb the free ligand, by precipitation of the antibody-isotope complex with ammonium sulfate or ethanol or by some other technique such as molecular sieve chromatography. The isotope antibody complex is recovered after centrifugation or collection of a specific column fraction and the radioactivity determined usually in an automatic beta or gamma counter. The amount of unknown substance present is determined from standard curves constructed from standards measured at the same time. Increasing additions of unknown sample reduces the specific activity of the isotope tracer thus yielding less radioactivity bound to the antibody.

The manual processing of samples for radioimmunoassay is time consuming, costly and requires meticulous attention to detail. In one laboratory alone, 8000 to 10,000 test tubes per month may be used for radioimmunoassay purposes. The repetitive nature and high precision of these determinations is responsible for considerable variability in the quality and reproducibility of the results. It is obvious that the complete automation of this technique would, of course, be desirable.

Several attempts to automate radioimmunoassays have only met with limited success.

For instance, in Johnson, U.S. Pat. No. 3,896,217, a method is provided wherein a sample containing an unknown concentration of a specific antigen, and containing a known concentration of the same antigen tagged with a radioactive isotope, is passed through a bed of an immobilized antibody which is specific in its reactivity for the antigen being detected. As the solution is passed through the bed, both tagged and untagged antigen are bound to the immobilized antibody. Since insufficient antibody is provided in the bed to react with all of the antigen in the solution, the solution passing through the antibody bed will contain both untagged and tagged antigen which is passed into a detector where the amount of unbound, tagged antigen present is measured. The bed is then washed with a regenerating solvent which extracts all of the bound antigen, and the released antigen is also passed into the detector for measurement of the quantity of tagged antigen which has been bound. The results are then correlated to a standard curve for determination of the concentration of untagged antigen in the original sample. This technique however, is not completely satisfactory since it requires a substantial time delay to effect extraction of the antigen which had been immobilized with the antibody, and consequently, is not completely amenable to rapid analysis, which would be necessary to effect analysis of a multiplicity of samples. In the Johnson technique, it is necessary to permit the antibody-antigen reaction to go to completion in order to get a viable static system. All of these requirements are time consuming operations.

Another approach to automated radioimmunoassay has been described by Ertingshausen et al (Clinical Chemistry 21, 1305, 1975). The technique involves the initial automatic pipetting of antibody and antigen reagents followed by precisely timed incubation of the mixed ingredients. Radioimmunoassays of samples are determined in a static system similar to other conventional techniques, and the concentration of antigen in the original sample is determined by the use of preobtained, standardized curves. This procedure is burdened with much the same manual operational procedure as other prior art techniques which do not permit the continuous and rapid determination of a multiplicity of antigen containing samples.

The conventional antigen measuring techniques have suffered from several disadvantages in that it has been difficult to determine in the measurement if a sufficient amount of antibody or isotopically tagged antigen is present to react with the expected quantity of antigen. Thus, valuable analysis time was often wasted by the necessity of waiting for results before it could be realized that insufficient antibody or tagged antigen is present for proper analysis. Moreover, the conventional procedures generally involve batch type analysis, which results in inefficient use of highly skilled labor and high costs of reagents.

A need therefore continues to exist for an automated radioimmunoassay technique for rapidly determining the concentration of a specific antigen in a sample by use of the antibody-antigen interaction.

SUMMARY OF THE INVENTION

Accordingly, one object of the present invention is to provide a fully automated and continuous assay method for the rapid and accurate determination of antigen through specific antibody-antigen interactions, using a novel radioimmunoassay technique.

Another object of the present invention is to provide an apparatus which is designed for the rapid, automatic radioimmunoassay of antigen by specific antigen-antibody reactions.

Briefly, these objects and other objects of the invention as hereinafter will become more readily apparent can be attained by use of an apparatus wherein a solution of a known concentration of antigen, tagged with a radioactive isotope, and a solution containing a known concentration of antibody is admixed with a sample containing an unknown concentration of antigen which is reactable with said antibody. The concentration of antibody solution is selected so as to be insufficient to react with all of the antigen present in the solution containing the tagged antigen. The mixture is permitted to incubate for a fixed predetermined time period, and it is then passed into a radioactivity detector means, wherein the radioactivity present in a fixed amount of mixed sample is kinetically detected. The mixed sample is then separated into an antibody-antigen complex containing portion, and an unreacted antigen containing portion. One of these solutions is then passed to a radioactivity detector and a second determination of radioactivity is measured. The ratio of radioactivity in the second measurement to radioactivity in the first measurement can be correlated to standard curves previously generated in the same way, and the quantity of antigen present in the unknown sample determined. One aspect of this technique is that the sample can be first read kinetically as it is passed through a radioactivity detector, thereby providing a factor which can be used to control for variables, loss of isotope during flow through the system or alteration in flow rate over a long period of time. The first kinetic measurement is also important in that it is used by the apparatus to determine when a sample is present for assay, i.e., when a predetermined threshold amount of radiation is detected, which thereafter sets off a sequence of control signals which controls the remainder of the assay process.

In this invention, novel apparatus is provided to effect the said radioimmunoassay, which comprises:

means for time controlled incubation of a multiplicity of sample solutions, each of which comprise a mixture of (a) a sample, possibly containing an antigen intended to be assayed, (b) a solution of a known concentration of an antigen tagged with a radioactive isotope and (c) a solution of a known concentration of an antibody reactable with said antigen;

radioactivity detector means for providing a kinetic measurement of radioactivity as a solution is continuously passed therethrough, and for providing a static measurement of radioactivity as a solution is maintained statically within said detector;

means for introducing said incubated sample into said radioactivity detector means;

timing means, which is activatable by said radioactivity detector means when said detector means detects a predetermined threshold of radioactivity, for measuring time sequences and for generating control signals at predetermined time sequences;

recording means coupled to said detector means for recording the amounts of radioactivity detected in said detector means;

means for separating said kinetically measured solution into a first portion containing antigen which is unreacted with said antibody;

means for introducing one of said portions from said separating means into said radioactivity measuring means, for static detection;

means for isolating said incubated sample from additional sample solutions introduced into said apparatus for assay, wherein said isolating means is activatable by a control signal emitted from said timing means, whereby said isolating means isolates the system at a first predetermined signal from said timing means, and whereby said isolating means reconnects the system to said incubation means at a second predetermined signal from said timing means, wherein the second predetermined time period is set so as to enable sufficient time to complete said static measurement before the next incubated sample arrives in the said detector means for the next sequential kinetic measurement; and means for flushing said sample from said system after static measurement thereof so as to prepare said detector for the next sequential sample for static measurement.

DETAILED DESCRIPTION OF THE PREFERRED EMBODIMENTS

Figure 1:
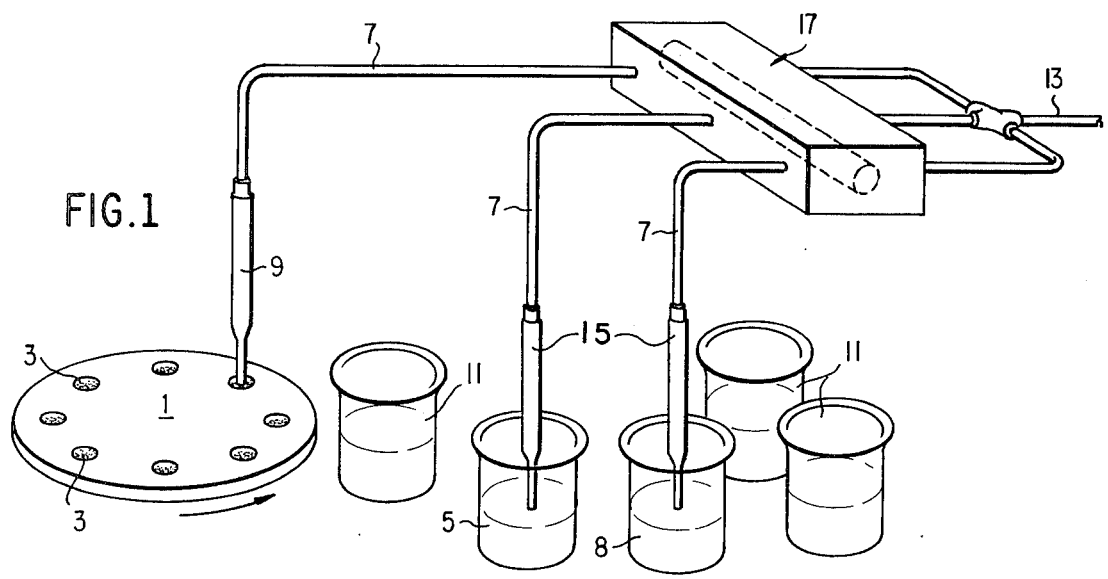
FIG. 1 is a schematic of a preferred sampling system used in this invention.
Figure 2:
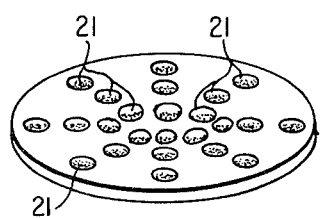
FIG. 2 is a schematic of an alternate disc sampler for use in the system of FIG. 1.

In the following description, the reference numerals refer to the numerals in the several Figures, as briefly described above.

According to the present invention, radioimmunoassay is carried out continuously and automatically, including reagent addition, separation of bound ligand from the total incubation mixture and radioactivity determination on line without any human intervention. The first results become available within 3–30 minutes, and in some instances, faster, and a new sample is thereafter processed every one and one-half to three minutes. One system according to the present invention can process over 400 samples per day, a rate which would be difficult to achieve by several technicians and several presently available conventional automatic radiation counters.

In the present invention, the antigen sample is mixed with a solution of an antigen which has been reacted with or "tagged" with a radioactive isotope, and with a solution of an antibody. The antigen sample may be one which has been obtained from such biological sources as blood, sera, plasma, ascites or the like, which is suspected of containing specific antigens. The antibody solution is obtained from known, commercial sources, and is selected specific to the specific antigen or antigens intended to be detected. The titer of the antibody in the antibody solution is known, and also the concentration of the antigen tagged with the isotope is known. The dilution of the antibody solution is selected so that insufficient antibody is present to react with the total quantity of antigen expected to be present in the system. The antibody can be used in this system in a very high dilution, as high as 1/500,000. It is somewhat surprising that the antibody remains sufficiently stable for the purposes of this system.

Isotopic tagging of the antigen can be effected by conventional techniques such as by reacting the antigen with moieties that will leave residual amounts of $^{125}I$ or $^{131}I$, or any other suitable radioactive isotope as is known in the art such as $^{75}Se$, $^{3}H$, $^{14}C$, or $^{32}P$.

The concentration of the tagged antigen solution can vary from one millimolar to the limits of concentrations of isotope detectable by the radioactivity detection, usually one picomolar. The dilution of the antisera in the antibody solution can be from 1:10 to 1:500,000, depending upon the characteristics of each respective antisera. Instead of a single antibody or a single antigen, two or a plurality of different tagged antigens and different antibodies can be used in combination to give a simultaneous multiple assay. Representative of the antibody-antigen systems which might be used include: $^{125}I$-Digoxin, $^{131}I$-Thyroxin, $^{125}I$-secretin, $^{32}P$-cyclic AMP, $^{131}I$-Insulin, $^{125}I$-Glucagon, $^{75}Se$-Cortisol, $^{125}I$-Angiotensin I, $^{125}I$-Carcinoembryonic antigen, $^{125}I$-Somatostatin, $^{131}I$-Insulin, $^{131}I$-Triiodothyronine, $^{125}I$-Thyroxin, $^{125}I$-Growth Hormone, $^{125}I$-cyclic AMP, $^{131}I$-cyclic GMP, $^{125}I$-Morphine, $^{125}I$-Vasopressin, $^{131}I$-Aldosterone derivative and their respective antibodies. The antigens and antibodies could be contained in sera, urine or other buffers commonly used in the presently known art of radioimmunoassay such as sodium acetate, Tris-HCl, Barbital, Phosphate, MES, TES, etc. The sample being assayed could be measured at several dilutions such as 1:1, 1:2, 1:5, 1:10, 1:100, 1:1000, etc.

The two solutions and the sample being assayed are stored in separate containers until ready for mixing. One especially good sampling system is a disc sampler as shown in FIG. 1. In this system, a rotatable disc 1 holds a multiplicity of small cups 3, a container of antibody solution 5, and solution containing antigen tagged with a radioactive isotope 8. The sample from one of the cups is withdrawn through pipette 9 which is on a raisable and rotatable bracket such that after a sample is extracted, the pipette is rotated upwardly and away from the cup, enabling the disc to rotate, bringing the next sequentially placed cup into alignment with the pipette 9. During the period of the rotation of the disc 1, and when samples are not being withdrawn, the pipettes 9 and 15 can be placed into container 11 which contains a buffer solution. In this manner, a space of buffer solution is ultimately provided in conduit 13 which separates adjacently moving samples. Antibody solution from source 5 and tagged antigen solution from source 8 are extracted by pipettes 15. Pick-up of the tagged solution is intermittent and pick-up of the antibody and samples can be intermittent or continuous. In other words, one can have a continuous feed of the sample and intermittent pick-up antibody, or can have continuous pick-up of antibody and intermittent feed of the sample. Thus, one can analyze the same sample solution with different antibodies, or one can analyze different samples with the same antibody. For example, one patient serum could be placed into stationary containers 5 or 8 and drawn coincidentally with a variety of antigen-antibody pairs placed on the rotating disc.

Suction for the operation of the pipettes 9 and 15 is provided by a vacuum created by a laminar flow type pump, such as a multichannel peristaltic pump 17. The sample and the solutions are drawn into conduits 7 and simultaneously mixed in conduit 13 for 1 to 30 seconds before being lead to incubator 19. Pick-up and mixing of a new sample solution can occur as often as once every one to three minutes.

Instead of two separate solution sources 5 and 8, a very neat package could be formed by having small cups or vials 21 placed into series on the rotatable disc 1. Thus, one cup would contain the sample and the other two of the three cup series would contain the other solutions. Thus, it might be possible to have one series of cups for measurement of insulin digoxin, another series of cups for measurement of thyroid, etc., possibly all for the same patient, wherein each series containing one cup of the same sample, which may contain a variety of antigens, or the system can be used for testing many samples from different patients in a continuous manner. Disc samplers are known and are disclosed in U.S. Pat. Nos. 3,902,371; 3,038,340; 3,424,557; 3,134,263 and 3,230,776.

Another alternative is to use a conventional fraction separator, instead of the disc sampler, to introduce the samples into the system.

After the solutions are mixed by the pumping action, the mixture is passed through conduit 13 and into an incubation chamber where the mixture will be held under standardized conditions for a fixed predetermined incubation time period.

Figure 4:
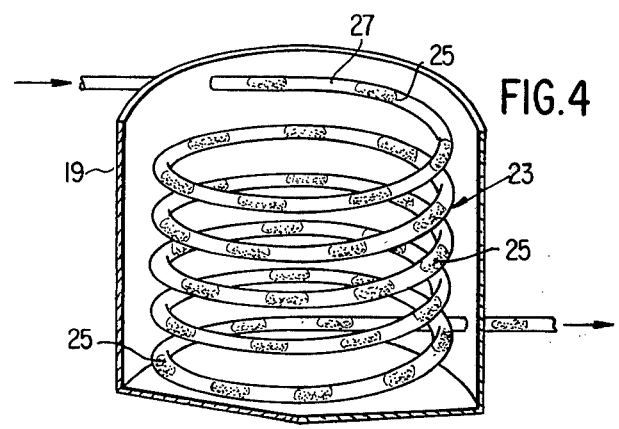
FIG. 4 is a schematic diagram of a suitable incubation system used in the apparatus of FIG. 3.

The incubation chamber may take many forms, however, one of the most advantageous is a long coil-like conduit 23 as shown in FIG. 4 which is held at a predetermined incubation temperature. The flow rate of the sample solution through the incubation may be adjusted so that the reaction is sufficiently completed by the time the sample solution traverses the length of the conduit. A multitude of sample solutions 25 can be present in the incubation conduit at the same time, each separated by a buffer solution space 27. The buffer space 27 not only separates sample solutions, but also picks up tailings so that the next succeeding sample will not be contaminated. Since the solutions in conduit 23 are moving in laminar flow, there is, of course, a potential flow problem with the fluid in the center of the tube moving at a faster rate than at the edges. This potential problem can be quite easily dissipated by intermittently introducing bubbles in regularly spaced intervals into conduit 13, through bubbler 14, which serves to move the fluid along at a more uniform rate. This technique is disclosed in Skeggs U.S. Pat. Nos. 2,797,149 and 2,879,141.

In one such system which has now been constructed, as many as 15 samples have been under varying stages of incubation at one time.

The incubation temperature will, of course, depend upon the particular antibody-antigen system under study. In general however, the incubation temperature may vary from 0° to 60° C, and often incubation can be effected at room temperature.

The flexibility of this system is quite excellent and the system may be used for continuous assay of different systems. Thus, each sample solution extracted and introduced into conduit 13 may contain a different antigen-antibody system. It is not even necessarily required to readjust the incubator conditions in many cases, each time the antibody-antigen system is changed. It is only necessary that the calibration of the equipment for standardized samples be made under the same conditions as those used for the unknown. That is to say, it is not necessary that the incubation period be sufficient for the reaction to go to completion. It is only necessary that the incubation period for the samples be the same as the calibration. This is in sharp contrast to prior systems which in general required the reactions to go to completion for success. Of course, the closer to completion and equilibrium the system is carried during incubation, the more sensitive will be the assay. The length of incubation may vary from 1 minute to 30 minutes and even up to 1 day, depending upon the particular system. In general, if the incubation time is unacceptably long, it is possible to speed incubation by the addition of more antibody or altering the temperature.

Alternatively, the sample can be moved into one of a plurality of containers which is held under predetermined incubation conditions after which a pipette or similar device removes the incubated sample from the container and moves it toward the isolating valve 31.

Figure 3:
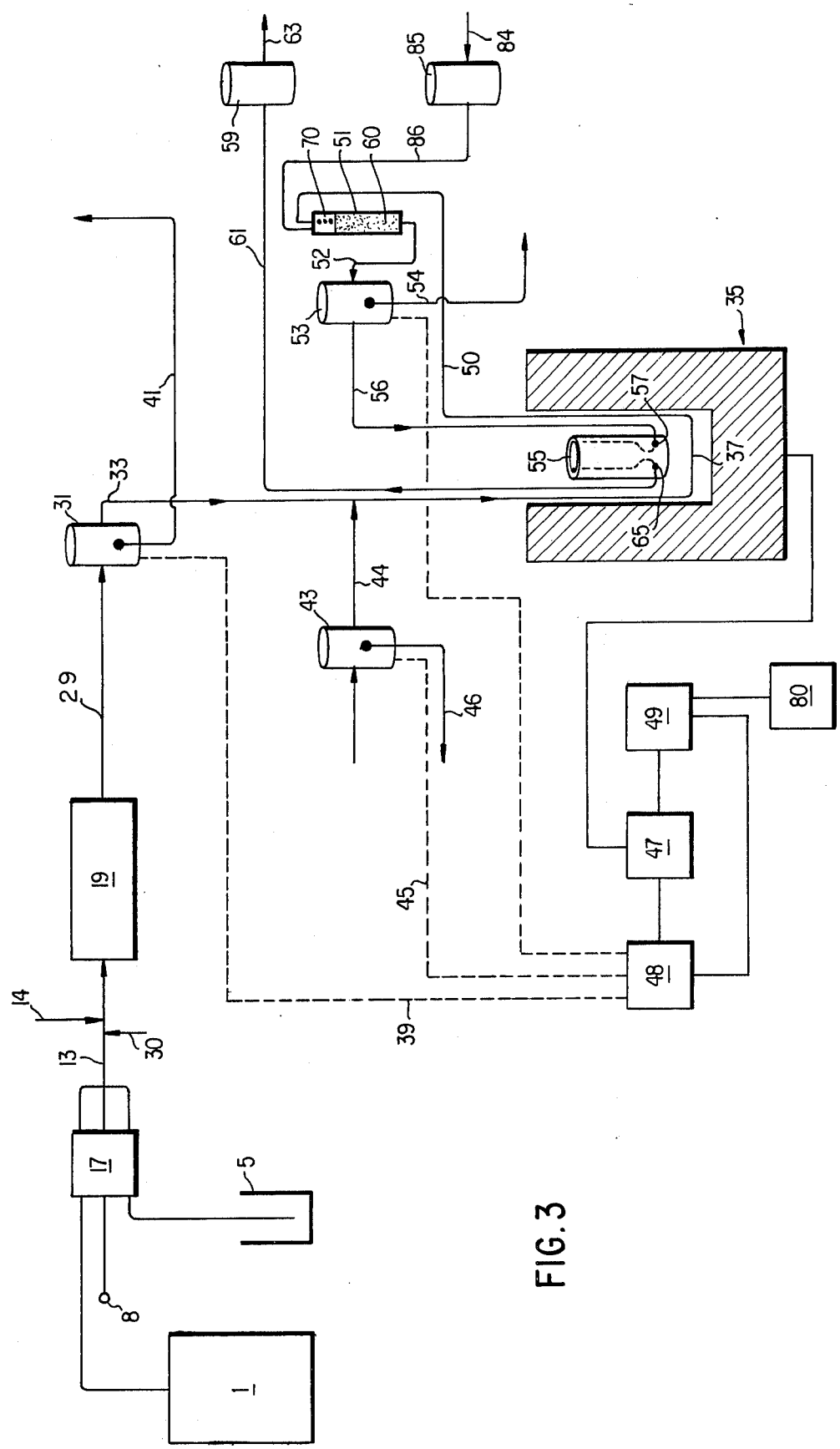
FIG. 3 is a schematic diagram of the apparatus of this invention.

At the termination of the incubation period, the sample is passed through conduit 29 as shown in FIG. 3 into an isolation valve or by-pass valve 31. The driving force for the movement of the sample through the system to this point is usually due to the pressure created by the peristaltic laminar flow pump.

The isolation by-pass valve 31 connects the conduit 29 with conduit 33 and, alternatively, with conduit 41 to waste. Conduit 33 leads to the radioactivity detector 35. At the start of the flow system, valve 31 is opened to conduit 33 and the incubated sample is directed into the radioactivity detector 35. As the incubated sample passes through the conduit 37 within the radioactivity detector 35, the amount of radiation is measured. The radioactivity detector used herein is conventional, and any suitable detector may be used such as a NaI gamma detector. Alternatively, a liquid scintillation counter, conventionally available may be used herein. The appearance of a threshold level of radioactivity in the detector triggers a predetermined timing sequence which begins scaling the sample for a predetermined period of time, usually 1 minute. This timing means 48 is set after a comparator circuit 47 indicates that the threshold of radiation is present. Control signals from the timing means 48 thereafter sets off various valves in a sequence necessary to cause the sample solution to be brought to a separator 51, where a portion of a free antigen and free isotope tagged antigen will be separated from a portion of antigen-antibody and tagged antigen-antibody complexes. Thereafter, one of the portions will be brought into a small reservoir cup 55 in a radioactivity detector and scaled for a predetermined time period, usually about one minute.

Thus, the radioactivity detector senses the sample, can determine how much sample has been applied to the column and finally accurately and with known statistics measures the amount of bound radioactivity. It is thereafter easy to compute the ratio of radioligand bound to total radioactivity in each sample and to construct standard curves from these ratios. Alternatively, standard curves can be constructed on the basis of only the bound radioactivity if flow characteristics are sufficiently constant and stable. The timing for each sample is thus exactly the same and is not influenced by small variations in the pumping rate, which can occur over long periods of time. A small variation in the amount of sample applied to the column is thus inconsequential because the bound/total ratio, which is computed for each sample does not depend upon constant sample radioactivity.

The timing means 48 measures predetermined time sequences after which it sends out control signals through line 39 to activate the isolation valve 31, which thereby isolates the measurement portion of the system from the incubation portion of the system. The time sequence measured before valve 31 is activated, is sufficient to at least enable the entire sample to pass into the detector 35 before the measurement system is isolated. In other words, the valve 31 will usually close at some point in time as buffer solution spaces 27, which separates adjacent sample solutions 25 to be measured, is passing through the valve 31.

One very interesting aspect of this invention is that the first radiation measurement is made as the sample is kinetically passing through the detector conduit. Usually a kinetically obtained measurement is considered to be too inaccurate for practical application. The present inventors, however have found that the kinetic measurement is proportional to the static measurement, and can be used to compensate for losses of isotopes in the system. The kinetic measurement is also sufficiently accurate to enable its use to control the apparatus, as in the present invention. A recording means 49 is provided which is coupled to the comparator circuit 47 and the timing means 48, which is used for recording the amount of radioactivity in the kinetic and subsequently the static measurements. These measurements will be compared to calibration standards for the ultimate determination of the amount of specific antigen in the unknown sample using a computer 80 which is interfaced to the recording means 49 and timing means 48.

After the isolation valve 31 is closed, thereby diverting the feed from conduit 29 into waste conduit 41, a means can be provided for increasing the speed of the sample solution. In FIG. 3, this means takes the form of a high flow rate buffer solution inlet valve 43 which is opened simultaneously as the isolation valve 31 is closed, by predetermined signal from timer 48 from line 45. A buffer solution at high speed enters through conduit 44 into the conduit 33. The high flow rate buffer solution pushes the sample solution through conduit 50 into and through a separator column 51. This high flow rate may be needed because the resistance of the separator column might otherwise prevent the free flow of the solution therethrough. The high speed turbulent buffer solution also acts to wash any tailings from the sample solution into a separator column, so as to prevent contamination of subsequent sample solutions and to speed the appearance of the isotope solution in the radiation detector. In general, the high flow line can feed buffer at a rate of 0.5 ml/min to 50 ml/min and preferably 3 ml/min to 10 ml/min, depending, of course, upon tube and valve size.

The flow rate through the separator column 51 is controlled by the hydrostatic head created by the outlet of conduit 54 when the air trap valve 85 is energized to connect conduit 86 with conduit 84 which is at atmospheric pressure. As demonstrated in FIG. 5, the air trap valve 85 is deenergized simultaneously as the high flow buffer inlet valve 43 is actuated and the isolation valve 31 is closed. This causes the hydrostatic pressure to increase in the column 60 and the rate of flow through the column 60 increases as it emerges through conduit 52. The flow rate now nearly equals the flow rate of the high flow buffer line 44.

The separator column 51 serves to separate the sample solution into two portions: a first portion containing the unreacted antigen and unreacted antigen which has been tagged with the isotope, and a second portion containing the antibody-antigen complex and the antibody-tagged antigen complex. This separation can be accomplished by a variety of means, some conventional and some not conventional. In one technique preferred by the present inventors, the separator is a column which is filled with an adsorbent 60 which adsorbs any antigen which is not bound to an antibody.

The types of adsorbents which are used to fill the column can be any material which selectively adsorbs free antigen in solution and will not adsorb the antigen-antibody complex. Suitable adsorbents for the column include anion and cation ion exchange resins such as Dowex 1, Dowex 2, Dualite A-2, DEAE cellulose, Amberlite CG-400, Permutit S-1, Dowex 50, Amberlite CG-50, CM-cellulose, DEAE-Sephadex, etc. Molecular sieves such as Sephadex G-10, G-25, G-50, G-75 or G-100, Bio-Gel P-20, P-30, P-60 or the like could also be used. In addition, a high concentration of specific antibody bound to a solid support could be used to adsorb unreacted radioactive antigen. In a preferred embodiment of the adsorbent, the column is packed with a region of charcoal and a region of an anion exchange resin. Usually the antigen carries a partial charge which enables it to be adsorbed into the ion exchange resin. If radioactive impurities are present in the radioactive antigen and they are uncharged, they will not adsorb onto the ion exchange resin, but will be adsorbed onto the charcoal. Moreover, frequently there are radioactive impurities which can be adsorbed by the ion exchange resin, but not on the charcoal. Consequently, by using both materials as adsorbents, less pure reagents can be used for this radioimmunoassay process. Since the adsorbent(s) in the column is capable of adsorbing unbound antigen from a multitude of samples, the adsorbent in the column does not require frequent changing. Instead of using the abovedescribed adsorbents in the column, it is possible to effect separation of unbound antigen from the bound complex by using a semipermeable membrane or a chromatography molecular sieve such as Sephadex. However, the use of membranes is not preferred because the separation by this technique is too slow.

In another embodiment of the adsorption process in the column, it is possible to reverse the adsorption process by adsorbing the bound antigen-antibody complex and allowing the free antigen to pass on through the column for measurement.

The residual sample is eluted from separator 51 by the high flow rate buffer and passes through conduit 52 into fill valve 53 which had been opened by a predetermined signal from timing means 48. Once the entire eluted portion passes through the fill valve 53, it is again closed, thereby diverting additional buffer coming from the separation column 51 to waste through conduit 54. In the case wherein molecular sieve chromatography is used to separate antibody bound radioligand from free radioligand, the antibody bound radioligand emerges from the separation column 51 first and is eluted from the separation column and through conduit 52, through fill valve 53 into the static counting chamber 55 before the free radioligand begins to emerge from the column. Once the antibody-bound radioligand has eluted from the column, the fill valve 53 closes and the free radioligand is eluted from the column through conduit 52 into valve 53 and to a waste receptacle through conduit 54. The column is now ready to receive the next sample. The portion being measured is thus passed into the static measurement section 55 of the radioactivity measurement detector 35 through conduit 56. The static measurement section 55 is shown in FIG. 3 as a cup having an inlet aperture 57 situated at the base thereof. The residual sample flows from valve 53 through line 56 and into the cup 55 through lower aperture 57. After the residual sample fills the cup, a radioactivity level count for a predetermined time which is controlled by timing means 48 is made and recorded by recorder 49.

At a predetermined time during the time interval when the radiation level is being determined, timing means 48 sends a control signal to by-pass valve 31 which reconnects conduit 29 with conduit 33 and permits the next sequential sample solution to begin its ascent to the detector 35. At a predetermined time after conduit 29 is reconnected with conduit 33, the timing means 48 sends a signal and valve 59 is opened, which connects conduit 61 with conduit 63 which is connected to a vacuum source developed by the peristaltic pump pumping against valve 59 through conduit 63. The solution in the cup 55 is thereby rapidly evacuated through exit port 65 and is disposed of. The control mechanism can be set, if desired, such that at the completion of one control sequence, and hence completion of analysis of one sample, the indication level must return to a predetermined minimum base line before the mechanism can be reactivated to begin the analysis of the next sample.

In the above-discussed arrangement, the inside walls of cup 55 may be made of a non-adhering material such as teflon or polyphenylenesulfide. Moreover, the design of the cup with the inlet and outlet apertures situated at the base of the cup functions to avoid splashing so that the cup will empty quite cleanly even without the introduction of the buffer wash solution. Simultaneous with the activation of valve 59, the timing means sends a signal to stop the recording means 49 and causes the recording means to transfer the accumulated counts to computer 80 for data processing as determined by the software programs. The recording means 49 then resets and is ready to record data for the next sample.

Figure 5:
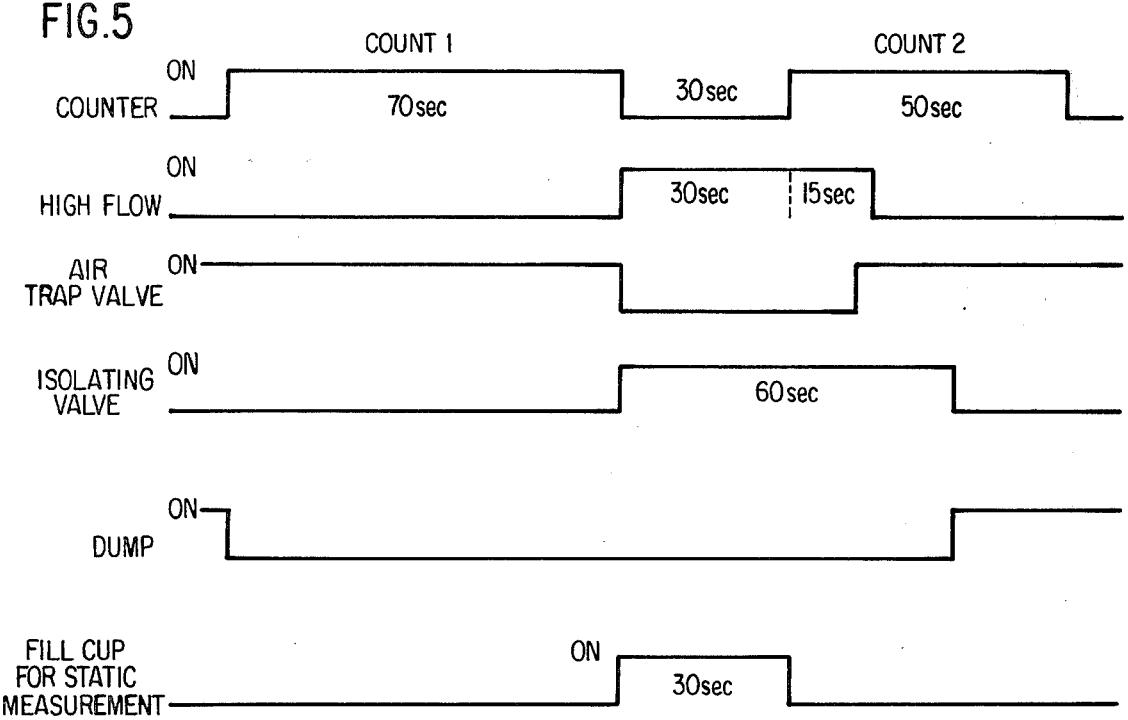
FIG. 5 is a timing diagram to show the sequence of valves opening and closing as required by the apparatus of FIG. 3.

Before the isolation valve 31 is reopened, the high flow rate buffer inlet port 44 is closed by a control signal from the timer. When the isolation valve 31 is reopened, connecting conduits 29 with 33, the pressure in conduit 33 approximates that in conduit 29 so that there is no sudden backwash through the incubation system. Similarly, when the by-pass valve 31 is in its closed position, thereby connecting conduits 29 with 41, the pressure in conduit 41 approximates that in conduit 33 since the outlets of conduit 41 and conduit 54 are physically held at the same hydrostatic pressure head. Thus, the flow rate of samples is not altered when valve 31 is energized or deenergized. A typical timing sequence for emitting control signals is shown in FIG. 5. Note that the difference in time between the shut off of the isolation valve 31 and the shut off of the high flow stream valve 43 and energizing of the column air trap valve 85 allows the conduit 33 to reach the same hydrostatic pressure as conduit 29 so that backflow or alteration in flow rate does not occur when the conduits 29 and 33 are reconnected. In addition, air space 70 above the column bed 60 is now at atmospheric pressure.

The analytical procedure of the present invention provides the analyst with the data for a ratio which is proportional to the bound radioactivity divided by the total radioactivity and expressed as follows:

$$\frac{\text{Static radioactive count of antigen-antibody complex}}{\text{Kinetic flow count of radioactivity in total sample}}$$

To obtain the concentration of the antigen in the original sample, the value of the ratio is compared to a pre-obtained curve obtained by plotting a series of measured ratios from standard solutions having known concentrations of antigen. The standard solutions are run through the test procedure under the same incubation time and temperature conditions to which the solutions to be analyzed are subjected, and the data obtained can be converted to ratios which are then plotted to form the graph of the standard curve. If the analytical process is shown to be constant with respect to all parameters of samples, antibody and isotope addition and other parameters essential for high reproducibility, then the second static count of the antigen (radioligand)-antibody complex can be used as the sole basis for calculation of the standard curve and subsequent test results.

The major advantage of the present method is that it provides a fully automated procedure for the measurement of antigen concentration in a test sample, in only a fraction of the time previously required by conventional radioimmunoassay techniques. The present method makes it possible to run a series of tests of widely varying antigen-antibody interactions without any disruption in continuous operation of the apparatus. Consequently, the system does not require the control of a skilled operator, and even unskilled labor can be used to perform the relatively simple tasks required to set up the present system. Since there are literally hundreds of drugs, hormones and biochemically important compounds currently measured by manual application of the radioimmunoassay such as analyses of digoxin, insulin, angiotensin I, thyroxin, cyclic AMP, and the like, the present method provides a means for rapidly and accurately conducting these analyses.

This system also allows the simultaneous detection of several antigens in the same sample. In this instance, several different isotopes are used with the different antigens. The radioactivity detector will thus detect the different levels of radioactivity emitted by each of the isotopes and by computerized selectivity, simultaneously determination of two or more antigens can be made.

Having generally described the invention, a more complete understanding can be obtained by reference to certain specific examples, which are included for purposes of illustration only, and are not intended to be limiting unless otherwise specified.

Assays for digoxin, cyclic AMP, cyclic GMP, insulin, angiotensin I and thyroxin are easily performed with this process. In these cases, the sample, isotope solution and antisera were drawn for 30 seconds with a 2½ minute wash between samples. The timing means was preset as shown in FIG. 5. Air bubbles were introduced at the rate of 0.32 ml/min into conduit 14. The conduit 63 was pumped at 3.9 ml/min to create suction to rapidly evacuate the static counting cell 55 when valve 59 was opened. Table I details the essential details of these assays with regard to reagents and flow rates. the coefficient of variation of these assays was about 2%.

TABLE I

REAGENTS FOR THE AUTOMATED RADIOIMMUNOASSAY

Flow Rate → 0.1 ml/min    0.1 ml/min    0.1 ml/min    0.23 ml/min    7.8 ml/min

| Compound (Sample | $^{125}$Radioligand (0.2 μCi/ml 5 | Antisera 8 | Separation Column 51 | Buffer Line 30 | High Flow 44 | Counts Collected for B | Time Delay Coil (min) | Temp. |
|---|---|---|---|---|---|---|---|---|
| Digoxin | Digoxigenin 3-O-Tyrosine | 1:30,000 | AG 1-X8 100–200 | Solution 1 plus 5 mg/ml bovine serum albumin | Solution 1 without Brij-35 | 3390 | 3 | Ambient |
| Cyclic AMP | ScAMP-TME | 1:2000 | mesh plus charcoal | | | 3325 | 21 | Ambient |
| Cyclic GMP | ScGMP-TME | 1:1000 | 60–200 mesh | | | 2153 | 21 | Ambient |
| Insulin | Monoiodinated Insulin | 2000 tube commercial antisera in 100 ml | or AG 1-X8 100–200 mesh 9×45 mm | Solution 2 | Solution 2 without Brij-35 | 1990 | 21 | 39° C |
| Angiotensin I | Monoiodinated Angiotensin I | 1: 2500 | | | | 2290 | 21 | Ambient |
| Thyroxin (T-4) | Thyroxin | 500 tube commercial antisera in 50 ml | | | | 1540 | 9 | Ambient |

Solution 1 is 50 mM sodium acetate, pH 4.7 containing 0.015% Brij-35. Solution 2 is 50 mM Tris-HCl, pH 9.2 containing 0.015% Brij-35. Thyroxin isotope solution also contained 1:5000 Sodium Merthiolate. Radioligand was dissolved in the Sampler Wash buffer. Antisera were diluted in the Buffer line buffer. ScAMP-TME (2'-O-Succinyl-Cyclic AMP Tyrosin Methyl Ester) and ScGMP-TME (2'-O-Succinyl-Cyclic GMP Tyrosine Methyl Ester) were labeled with [$^{125}$I]. Specific activity was between 100–200 Ci/mmole. [$^{125}$I]-Digoxigenin-3-O-Tyrosine (Sp.act. 150 Ci/mmole) Monoiodinated Insulin (100 μCi/ μg), moniodinated Angiotensin I (687 μCi/ μg), Throxin [$^{125}$I] (118 μCi/μg) diluted in either solution 1 or 2.

EXAMPLE 1

Figure 6:
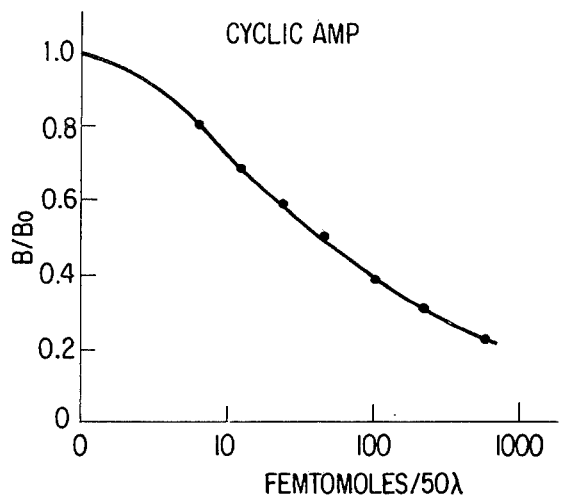
FIG. 6 is a standard curve for cyclic AMP.

FIG. 6 shows a standard curve for cyclic AMP after the standards had been acetylated (500 μl standard + 10 μl triethylamine + 5 μl acetic anhydride). This data and all following data for standard curves is plotted with the concentration of ligand being measured on the abscissa (log) vs the ratio of radioactivity found for standards to that when only the radioligand was present and is presented as the $B/B_0$ ratio. Whether or not the results are normalized by correction using the first count (count 1) the end result is the same, since the first counts would be the same if perfect pumping reproducibility occurred. This compound is thought to be an important mediator of hormone action.

EXAMPLE 2

Figure 7:
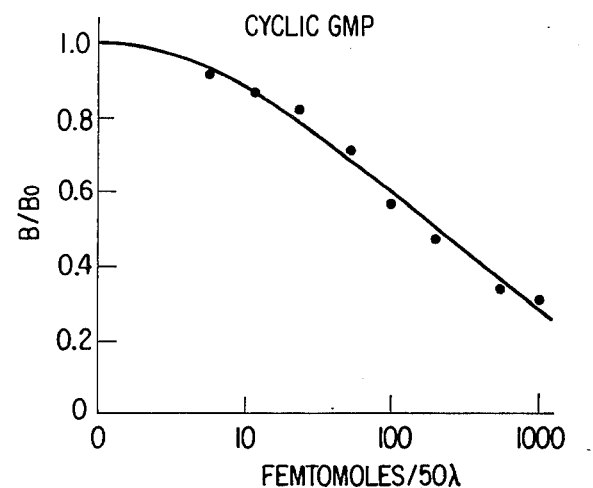
FIG. 7 is a standard curve for cyclic GMP.

FIG. 7 demonstrates a standard curve for cyclic GMP after the standards have been acetylated. It has been suggested that cyclic GMP could be an important regulator of processes controlled by the parasympathetic nervous system. In addition, some workers feel that cyclic GMP could be an important indicator of cell growth and its presence in urine could be used to detect certain organs malignancy. The sensitivity shown here is sufficient to measure cyclic GMP in less than 1 microliter of human urine.

EXAMPLE 3

Figure 8:
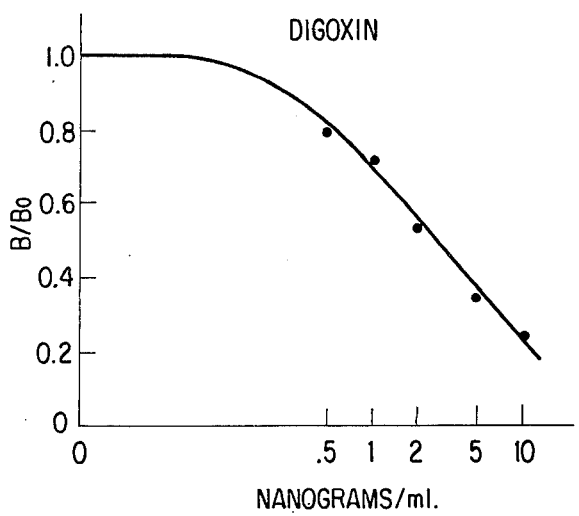
FIG. 8 is a standard curve for Digoxin.
Figure 9:
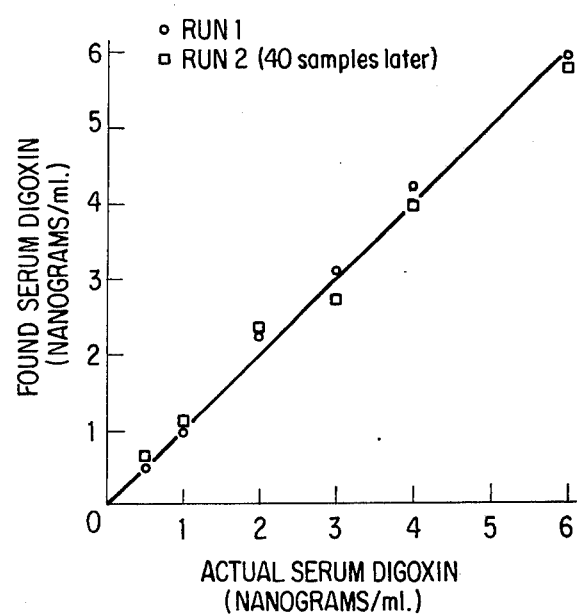
FIG. 9 is a comparison of commercial Digoxin standards with standards determined by the present invention.

FIG. 8 reveals a standard curve for digoxin. It takes less than 4 minutes to do a single determination. Digoxin is an important cardiac glycoside taken by between 3–5 million people in the USA alone. The drug markedly stimulates the heart in people with congestive heart failure. However, the drug is also very toxic to the heart causing rhythm disorders. Serum digoxin levels of 1.4 Ng/ml are considered therapeutic while toxic levels are considered when the serum level rises about about 2.5–3 Ng/ml. As can be seen, the assay method has sufficient sensitivity to make this distinction. When commercial serum digoxin standards were repetitively assayed, an excellent correlation was found as shown in FIG. 9. In addition, this Figure demonstrates the excellent instrument stability over a long period of time.

EXAMPLE 4

Figure 10:
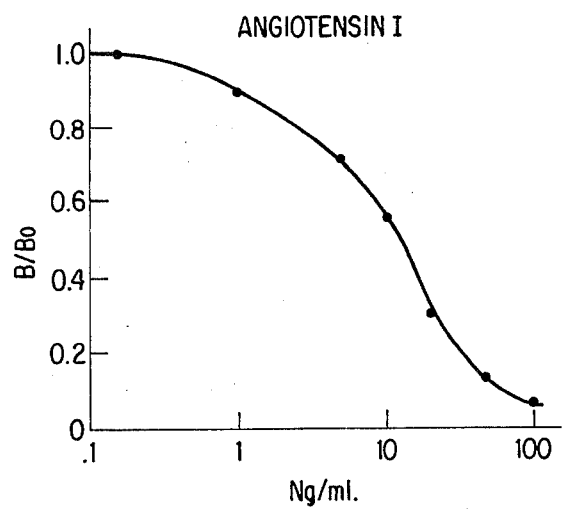
FIG. 10 is an Angiotensin I standard curve.

FIG. 10 illustrates a standard curve for Angiotensin I. While plasma levels are very low, the raidoimmunoassay for Angiotensin I is very useful to measure plasma renin activity (PRA). Normal PRA is about 1–6 Ng/ml Angiotensin I/hour and abnormal from 10–100 Ng/ml Angiotensin I/hour. It can be seen that the method can easily make this distinction.

EXAMPLE 5

Figure 11:
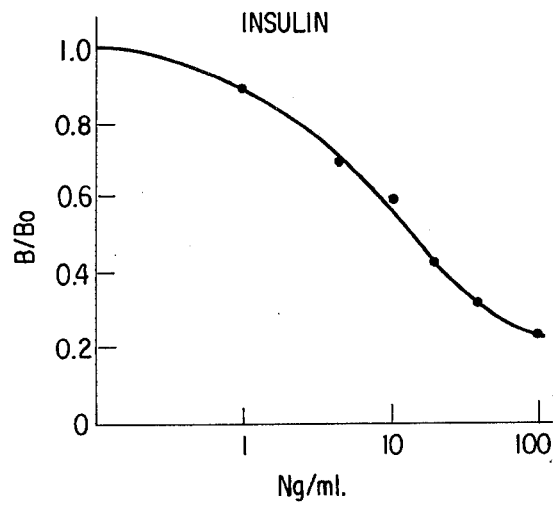
FIG. 11 is an insulin standard curve.

Insulin is an important hormone in glucose homeostasis. Measurement of serum or plasma insulin can be of aid in the diagnosis and management of patients with diabetes. The assay of insulin normally takes several days using conventional techniques. FIG. 11 demonstrates a standard curve for insulin. The total assay time for an individual insulin sample in the present system is only 21 minutes. This could be useful in cases where it is critical to know the serum insulin concentration in order to develop a therapeutic plan for a diabetic patient in insulin imbalance. The sensitivity of this assay is sufficient to monitor insulin in the concentrations normally encountered in clinical medicine.

EXAMPLE 6

Figure 12:
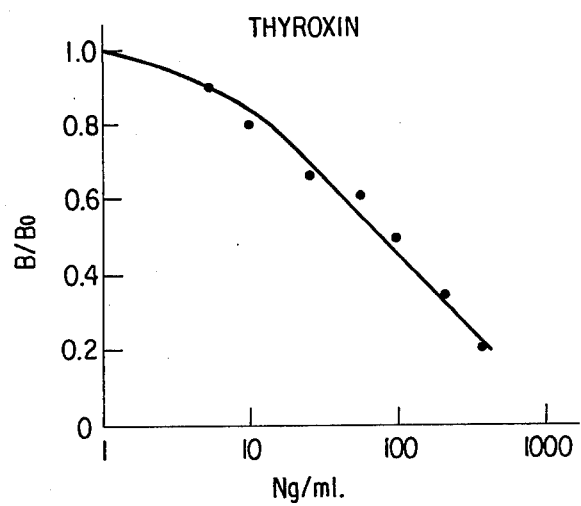
FIG. 12 is a thyroxin standard curve.

FIG. 12 demonstrates a standard curve for thyroxin. The sensitivity of the automated assay is comparable to other radioimmunoassays for thyroxin.

EXAMPLE 7

The automated radioimmunoassay system of the present invention is especially versatile being able to alternately sequentially assay for different samples. The following nine substances at the concentrations indicated were placed in the sample tray and their respective isotope solutions were drawn as each sample was processed. Incubation was for 21 minutes at 39° C. No delay between samples occurred and it took 27 minutes for all nine samples to be drawn into the instrument. Notice the excellent reproducibility and the ability to switch between different antigens without any equilibration time needed.

TABLE II

| Sample No. | Compound | Ng/ml | $B/B_0$ |
|---|---|---|---|
| 1 | Angiotensin I | 0 | 1.00 |
| 2 | Angiotensin I | 25 | 0.23 |
| 3 | Insulin | 0 | 1.00 |
| 4 | Thyroxin | 0 | 1.00 |
| 5 | Insulin | 25 | 0.45 |
| 6 | Thyroxin | 0 | 1.05 |
| 7 | Insulin | 25 | 0.42 |
| 8 | Angiotensin I | 25 | 0.20 |
| 9 | Insulin | 0 | 0.95 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. An automated radioimmunoassay apparatus which comprises:
   means for time controlled incubation of a multiplicity of sample solutions, each of which comprise a mixture of (a) a sample, possibly containing an antigen, intended to be assayed, (b) a solution of a known concentration of an antigen tagged with a radioactive isotope, and (c) a solution of a known titer of an antisera containing antibodies reactable with said antigen;
   radioactivity detector means for providing a kinetic measurement of radioactivity as a solution is continuously passed therethrough, and for providing a static measurement of radioactivity as a solution is maintained statically within said detector;
   means for introducing said incubated sample into said radioactivity detector means;
   timing means, which is activatable by said radioactivity detector means when said detector means detects a predetermined threshold of ratioactivity for measuring time sequences and for generating control signals at predetermined time sequences;
   recording means coupled to said detector means for recording the amounts of radioactivity detected in said detector means;
   means for separating said kinetically measured solution into a first portion containing antigen which is unreacted with said antibody, and a second portion containing antigen reacted with said antibody;
   means for introducing one of said portions from said separating means into said radioactivity measuring means, for static detection;

means for isolating said incubated sample from additional sample solutions introduced into said apparatus for assay, wherein said isolating means is activatable by a control signal emitted from said timing means, whereby said isolating means isolates the system at a first predetermined signal from said timing means, and whereby said isolating means reconnects the system to said incubation means at a second predetermined signal from said timing means, wherein the second predetermined time period is set so as to enable sufficient time to complete said static measurements before the next incubated sample arrives in the said detection means for the next sequential kinetic measurement of radioactivity.

2. The apparatus of claim 1, wherein said recorder means records the amount of radioactivity in the sample as it is passed kinetically through said detector, and wherein the assay results are obtainable from said recorder as a ratio of said static measurement to said kinetic measurement.

3. The apparatus of claim 1, wherein said detector means comprises a first section which is capable of detecting radioactivity amounts as a sample is kinetically passed therethrough and a second section which is capable of detecting radioactivity amounts as a sample solution is held in a substantially static position.

4. The apparatus of claim 1, wherein means are provided for increasing the rate of flow of the said incubated sample through said separating means, said means being activated by a signal from said timing means after said kinetic measurement.

5. The apparatus of claim 1, which further comprises: means for retaining said sample (a); means for retaining said solution (b) containing a known concentration of said tagged antigen; and means for retaining said solution (c) of known concentration of said antibody; and pumping means for withdrawing and mixing liquid portions from each of said retaining means to form said sample mixture and for propelling said sample solution into said time controlled incubator means.

6. The apparatus of claim 5, wherein said means for retaining the sample (a) is a disc, said disc holding a plurality of sequentially placed cups, and wherein said disc is rotatable so that each of said cups can sequentially be brought to a feeding position, and wherein a pipette, coupled to said pumping means, is situated at said feeding position, said pipette being movable between a first position wherein said pipette is dipped into said cup brought to said feeding position, and a second position wherein said pipette is incapable of receiving a sample, but which does not hinder the rotation of said disc, wherein as each sequential sample is desired to be introduced into the system, said disc is rotated to said feeding position for the next sequentially placed cup and said pipette is brought to its feeding position wherein a sample from the cup is extracted into said pipette as a result of a vacuum created in said pipette by said pumping means.

7. The apparatus of claim 6, wherein said disc holds a plurality of sequentially placed series of cups, each series comprising a cup containing said sample to be assayed, a cup containing said solution of tagged antigen and a cup containing said solution of antibody, and wherein said disc is rotatable so that each of said series is brought to said feeding position, and wherein an equal number of pipettes as the number of cups in said series is provided, each being coupled to said pumping means, such that after the disc is rotated to said feeding position, each of said pipettes is brought into one of the cups of said series so that feeding from the series occurs simultaneously, and wherein the pipetted solutions and samples are mixed and fed to said time controlled incubation means by said pumping means.

8. The apparatus of claim 1, wherein said time controlled incubation means is a cup wherein the said sample solution is deposited for a predetermined period of time before being introduced into said radioactivity detector means by said introduction means.

9. The apparatus of claim 1, wherein said introduction means is a temperature controlled conduit through which the sample solution is passed which is of a length such that as the solution is passed therethrough at a predetermined speed controlled by said pumping means, incubation is sufficiently completed.

10. The apparatus of claim 9, wherein a multiplicity of sample solutions to be assayed are introduced sequentially into said conduit such that incubation of said multiplicity of samples occurs simultaneously and in sequence.

11. The apparatus of claim 10, wherein each of said samples are separated by introduction of a buffer solution between each successive sample, wherein said buffer solution is fed to said conduit by a buffer feed means.

12. The apparatus of claim 5, wherein said pumping means is a peristaltic pump.

13. The apparatus of claim 12, which further comprises bubbler means positioned between said pumping means and said incubation means for intermittently injecting bubbles of air into said liquid steam emanating from said pumping means in order to provide a more uniform flow of liquid through said incubation means.

14. The apparatus of claim 13, which further comprises means for removal of bubbles from said sample after said sample passes said incubation means.

15. The apparatus of claim 1, wherein said isolation means comprises a valve which is rotatable between first and second positions, and which connects a conduit from said incubation means with a conduit to said radioactivity detector means, and with a conduit to waste, wherein in said first position, said conduit connects with said conduit to said waste, and wherein a pressure control means is provided such that the pressure within said conduit for said incubation means is maintained relatively constant irrespective of whether said valve is in its first or second positions.

16. The apparatus of claim 1, wherein said radioactivity detector means is a gamma detector.

17. The apparatus of claim 3, wherein said second section comprises a cup for retention of a solution, wherein said cup has inlet and outlet ports situated at the bottom thereof to permit filling and evacuation of said cup with minimal splashing of solution onto the walls thereof.

18. The apparatus of claim 1, wherein said separating means is a packed, continuous flow column containing an adsorbent which selectively adsorbs antigen which has not been reacted with antibody during said incubation.

19. The apparatus of claim 18, wherein said adsorbent is separated into a first zone which is packed with charcoal and a second zone which is packed with an ion-exchange resin.

20. The apparatus of claim 1, wherein said separating means is a continuous flow column containing an adsorbent which selectively adsorbs said antigen-antibody reaction complex formed during said incubation.

21. The apparatus of claim 1, wherein said means for increasing the rate of flow of the said incubated sample is a means for introducing a relatively high flow rate of buffer solution into the conduit carrying the incubated sample which moves the sample into, and through, the said separating means, and which simultaneously moves tailings into said separating means.

22. A method for continuous radioimmunoassay, which comprises:

incubating for a predetermined time period, a multiplicity of sample solutions, each of which comprises a mixture of (a) a sample possibly containing an antigen intended to be assayed, (b) a solution of a known concentration of an antigen tagged with a radioactive isotope, and (c) a solution of a known titer of antisera containing antibodies reactable with said antigen, the concentration of said antibody being selected so as to form an incubated sample containing an antibody-antigen complex, and containing unreacted antigen and tagged antigen, if said sample contains an antigen;

directing said incubated sample into a radioactivity detector which is capable of providing a kinetic measurement of radioactivity as the solution is continuously passed therethrough;

comparing the amount of radioactivity in said concentrated sample with a predetermined threshold and activating a timing means when said threshold is exceeded;

isolating said incubated sample from any additional samples being incubated on a predetermined signal from said timing means;

separating said incubated solution into a first portion containing unreacted antigen and tagged antigen and a second portion containing antibody-antigen and antibody-tagged antigen complexes;

directing one of said portions into a radioactivity detector, detecting the amount of radioactivity in said portion while said portion is maintained in a virtually static condition, and recording said measurement;

evacuating said portion to waste;

directing a subsequent incubated sample into said radioactivity detector on a second predetermined signal from said timing means so that the next subsequent incubated sample to be assayed arrives in the radioactivity detector for the next kinetic measurement after the previous static radioactivity measurement is completed; and comparing the ratio of the static radioactivity measurement to the kinetic measurement with a precalibrated ratio to determine the quantity of antigen being assayed.

23. The continuous method of claim 22, wherein said incubated sample is isolated, the flow rate of the incubated sample through a separation means is increased by a means activatable by a predetermined signal from said timing means.

24. The continuous method of claim 22, wherein said sample solution is passed in laminar flow through a conduit maintained at controlled incubation temperature, and wherein bubbles are intermittently introduced into the said conduit to assure uniform movement of the sample solution through the conduit, and wherein the bubbles are released at the termination of the incubation procedure.

25. The continuous method of claim 22, wherein said incubated sample is directed through a conduit through an isolation valve which isolates the sample from any additional incubating samples, and into the said radioactivity detector, wherein the conduit leading to the isolating valve is maintained at selected constant pressure.

26. The continuous method of claim 22, wherein the separation of the first and second portions is effected in an adsorption column wherein the antigen and isotope tagged antigen are adsorbed and the antigen-antibody complex and tagged antigen-antibody complex are permitted to flow therethrough.

27. The continuous method of claim 26, wherein said adsorption column is a combination of a first section which is packed with charcoal and a second section which is packed with Dowex 1 anion exchange resin.

28. The method of claim 26, wherein the column adsorbent is charcoal.

29. The method of claim 26, wherein the column material is a Sephadex type molecular sieve.

30. The continuous method of claim 23, wherein the flow rate of the incubated sample through the separation means is increased by injecting a high flow rate stream of buffer solution into the said conduit leading to the radioactivity detector.

31. The continuous method of claim 24, wherein said multiplicity of sample solutions form a continuus stream wherein each sample solution is isolated by portions of a buffer solution which is introduced between each sample solution within said incubation conduit.

32. The continuous method of claim 22, wherein sequential sample solutions being assayed contain different antibody-antigen systems.

33. The continuous method of claim 32, wherein sequential sample solutions being assayed contain the same sample from the same sample source, but contain different antibody and tagged antigen solutions so that sequential assays are accomplished for different antigen contents for the same patient sample.

* * * * *

UNITED STATES PATENT AND TRADEMARK OFFICE
CERTIFICATE OF CORRECTION

PATENT NO. : 4,022,577
DATED : May 10, 1977
INVENTOR(S) : GARY BROOKER, ET AL.

It is certified that error appears in the above—identified patent and that said Letters Patent are hereby corrected as shown below:

Claim 9, line 1 - delete "introduction" and insert "incubation".

Signed and Sealed this

Fourth Day of April 1978

[SEAL]

Attest:

RUTH C. MASON
Attesting Officer

LUTRELLE F. PARKER
Acting Commissioner of Patents and Trademarks